(12) United States Patent
Drake

(10) Patent No.: US 6,573,992 B1
(45) Date of Patent: Jun. 3, 2003

(54) PLANO CONVEX FLUID CARRIER FOR SCATTERING CORRECTION

(75) Inventor: David A. Drake, Escondido, CA (US)

(73) Assignee: Pointsource Technologies, LLC, Escondido, CA (US)

(*) Notice: Subject to any disclaimer, the term of this patent is extended or adjusted under 35 U.S.C. 154(b) by 0 days.

(21) Appl. No.: 10/062,247

(22) Filed: Jan. 31, 2002

Related U.S. Application Data

(60) Provisional application No. 60/332,403, filed on Nov. 13, 2001.

(51) Int. Cl.[7] ................................. G01N 21/00
(52) U.S. Cl. ....................... 356/338; 356/343
(58) Field of Search ................ 356/337–343, 356/244, 246

(56) References Cited

U.S. PATENT DOCUMENTS

| | | |
|---|---|---|
| 3,770,351 A | 11/1973 | Wyatt |
| 3,901,602 A | 8/1975 | Gravatt, Jr. |
| 4,070,113 A | 1/1978 | Frazer et al. |
| 4,173,415 A | 11/1979 | Wyatt |
| 4,265,538 A | 5/1981 | Wertheimer |
| 4,548,500 A | 10/1985 | Wyatt et al. |
| 4,565,448 A | 1/1986 | Abbott et al. |
| 4,728,190 A | 3/1988 | Knollenberg |
| 4,906,094 A | 3/1990 | Ashida |
| 4,942,305 A | 7/1990 | Sommer |
| 4,952,055 A | 8/1990 | Wyatt |
| 5,125,737 A | 6/1992 | Rodriguez et al. |
| 5,247,340 A | 9/1993 | Ogino |
| 5,414,508 A | 5/1995 | Takahashi et al. |
| 5,436,465 A | 7/1995 | Borden et al. |
| 5,534,999 A | 7/1996 | Koshizuka et al. |
| 5,737,078 A | 4/1998 | Takarada et al. |
| 5,835,211 A | * 11/1998 | Wells et al. ............... 356/336 |
| 5,999,256 A | 12/1999 | Jones et al. |
| 6,023,324 A | 2/2000 | Myers |
| 6,100,541 A | 8/2000 | Nagle et al. |
| 6,118,531 A | 9/2000 | Hertel et al. |
| 6,120,734 A | 9/2000 | Lackie |

* cited by examiner

Primary Examiner—Michael P. Stafira
(74) Attorney, Agent, or Firm—Leon D. Rosen

(57) ABSTRACT

A system for identifying microorganisms and other microscopic particles in a fluid, includes a laser that directs a laser beam (14) through a detect zone (20) and a plurality of photodetectors (30) that detect light scattered in different directions from a particle at the detect zone. The system includes a glass carrier (110) that confines fluid to movement along a narrow passage (116) in the carrier. The front surface (130) of the passage is flat, to facilitate prediction of the scatter light paths, and to enable the passage to have a small cross-sectional area.

9 Claims, 5 Drawing Sheets

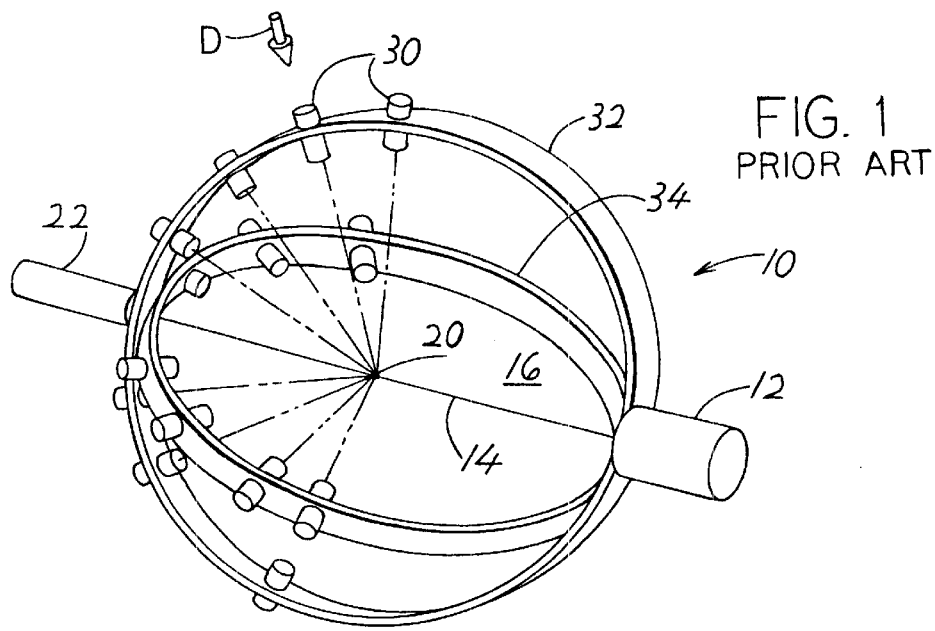
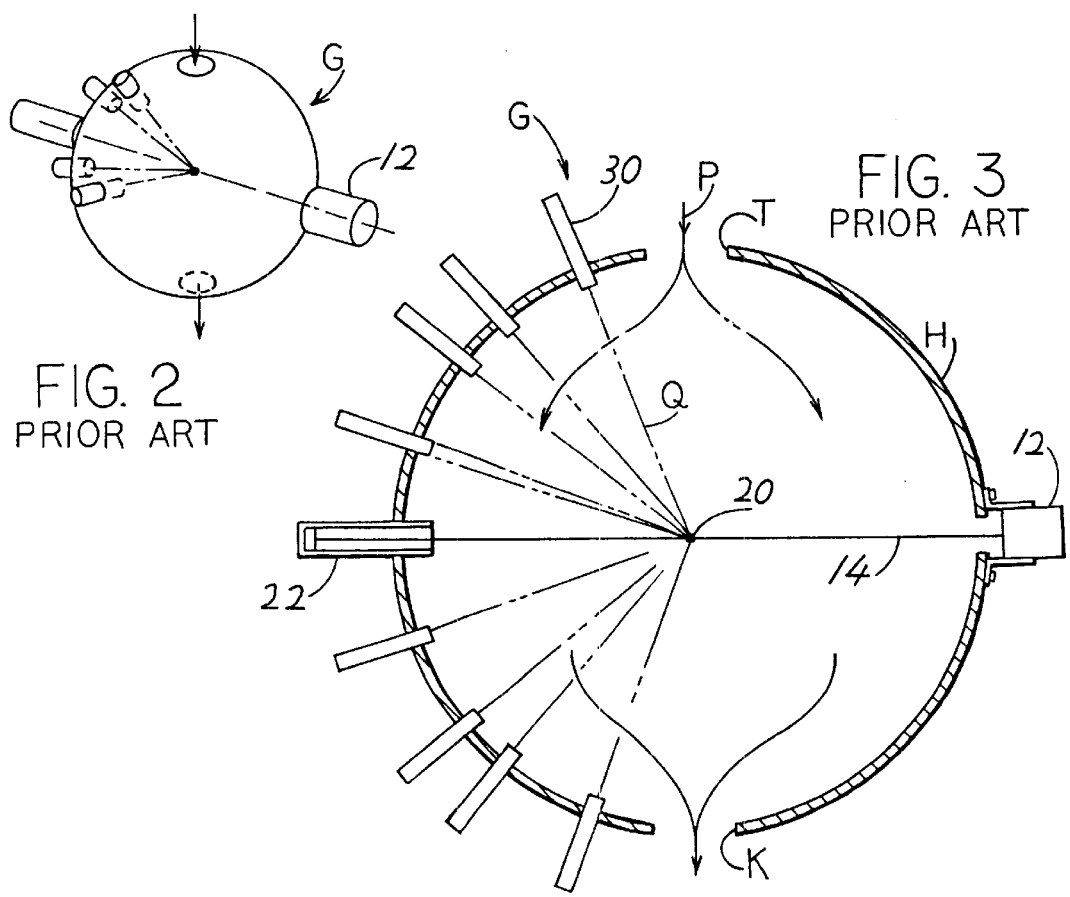

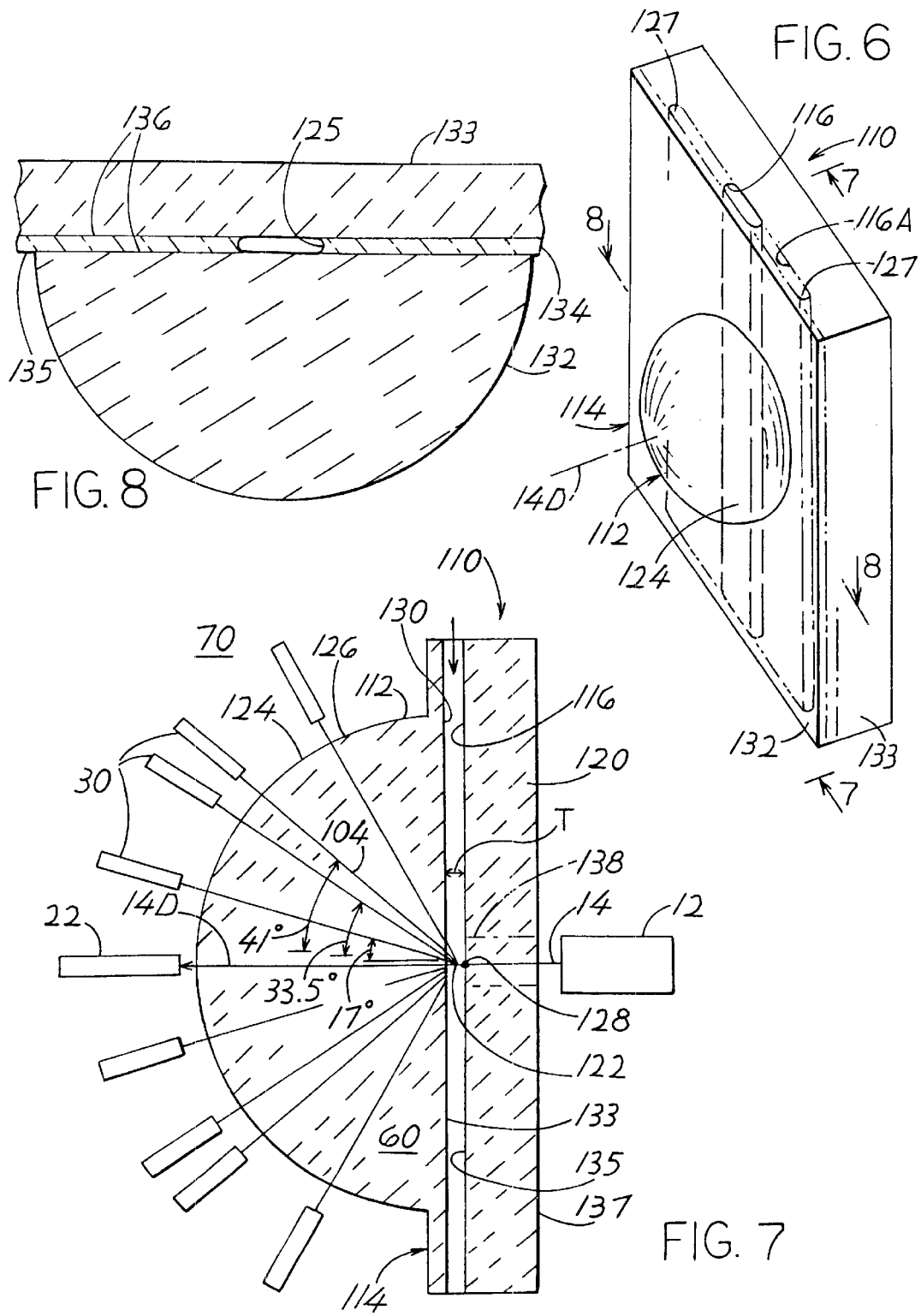

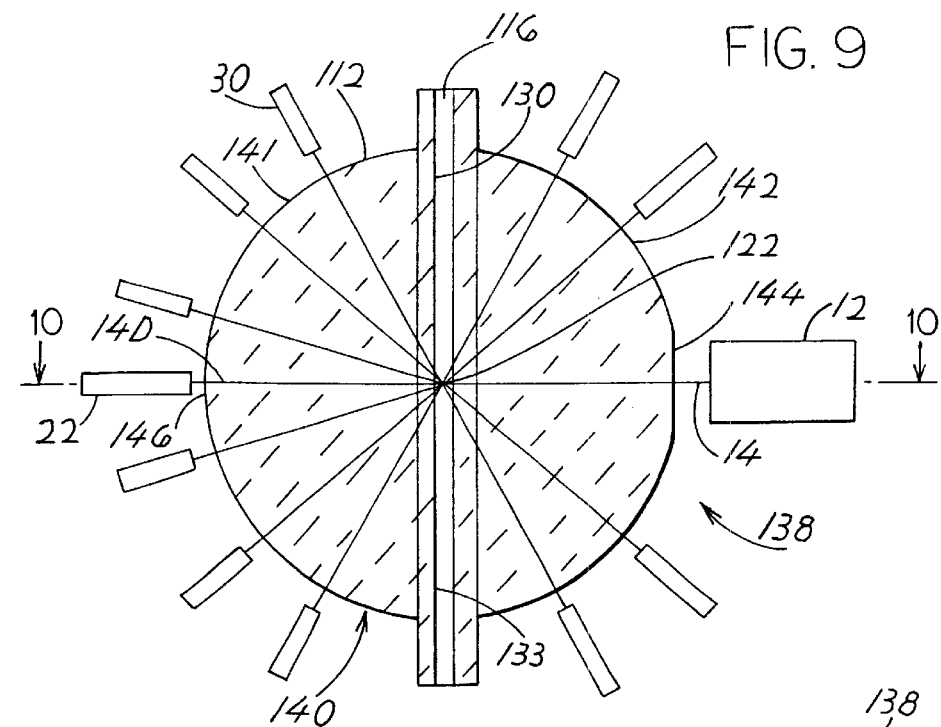
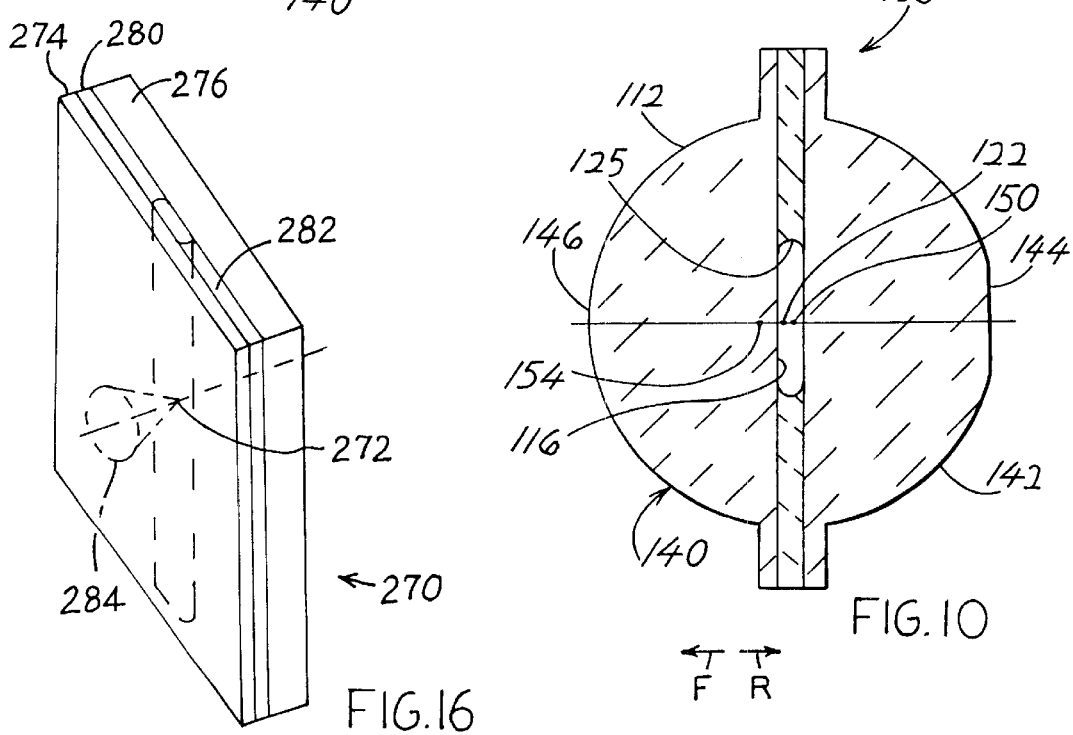

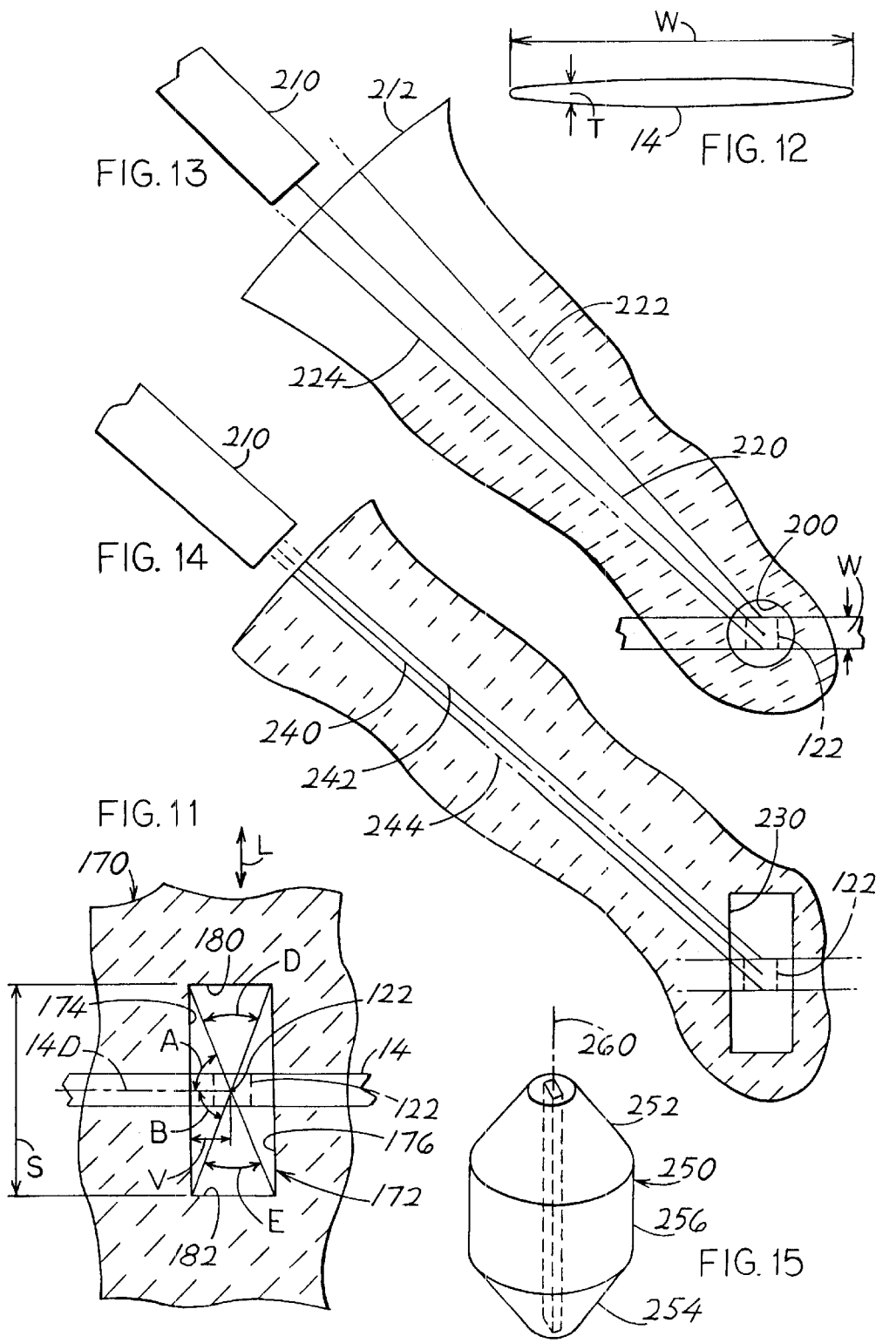

PLANO CONVEX FLUID CARRIER FOR SCATTERING CORRECTION

CROSS-REFERENCE

Applicant claims priority from U.S. provisional application Ser. No. 60/332,403 filed Nov. 13, 2001.

BACKGROUND OF THE INVENTION

Microscopic particles such as a particular specie of bacteria lying in a fluid such as water or air, can be identified by detecting its pattern of light scatter when it passes through a light beam. A plurality of photodetectors detect light scattered in different directions from a light beam. Although a laser that generates the light beam and multiple photodetectors that detect scattered light can be immersed in a contaminated fluid, this has a disadvantage that the laser and photodetectors may be coated with a slime or other material in the fluid and may become contaminated so that they require decontamination before they are handled. A system which enabled detection and/or identification of microscopic particles by a light source such as a laser and by multiple photodetectors, which isolated the laser and photodetectors from the fluid, would be value. It would be desirable in many applications, if a considerable portion of the fluid was directed through the light beam rather than around it.

SUMMARY OF THE INVENTION

In accordance with one embodiment of the present invention, an apparatus is provided for detection and/or identification of microscopic particles in fluid by detecting light scattered by a particle as it passes through a light beam, which confines fluid flow to a path of small cross-section. The apparatus includes a solid transparent material such as glass having a passage through which fluid flows and having an outside surface where photodetectors are positioned. The passage has a flat front surface. This allows a passage of small cross-sectional area to be used while the photodetectors accurately detect light scattered from a particle lying in a small detect zone located along the light beam.

The novel features of the invention are set forth with particularity in the appended claims. The invention will be best understood from the following description when read in conjunction with the accompanying drawings.

BRIEF DESCRIPTION OF THE DRAWINGS

FIG. 1 is an isometric view of a largely prior art particle identification system.

FIG. 2 is an isometric view of a prior art system.

FIG. 3 is a sectional side view of the prior art system of FIG. 2.

FIG. 6 is an isometric view of a system of another embodiment of the invention, wherein the carrier has a largely spherical outside shape and has a passage with a flat front surface.

FIG. 7 is a sectional view of the carrier of FIG. 6, taken on line 7—7 thereof, and showing the paths of light scattered from a particle in water.

FIG. 8 is a partial sectional view taken on line 8—8 of FIG. 6.

FIG. 9 is a sectional side view of a carrier of another embodiment of the invention.

FIG. 10 is a sectional view taken on line 10—10 of FIG. 9.

FIG. 11 is a partial sectional view of a carrier of another embodiment of the invention, wherein the carrier passage has a small width and length.

FIG. 12 is a sectional view of the laser beam of FIG. 11, taken at the detect zone.

FIG. 13 shows the paths of light scattered from the detect zone that lies along the beam of FIG. 12, for a carrier having a passage of cylindrical shape and of small diameter and a carrier outer surface of large diameter, compared to the beam width.

FIG. 14 is a view similar to that of FIG. 13, but with the passage having a flat front surface.

FIG. 15 is an isometric view of a carrier of another embodiment of the invention.

DESCRIPTION OF THE PREFERRED EMBODIMENTS

Figure 4:
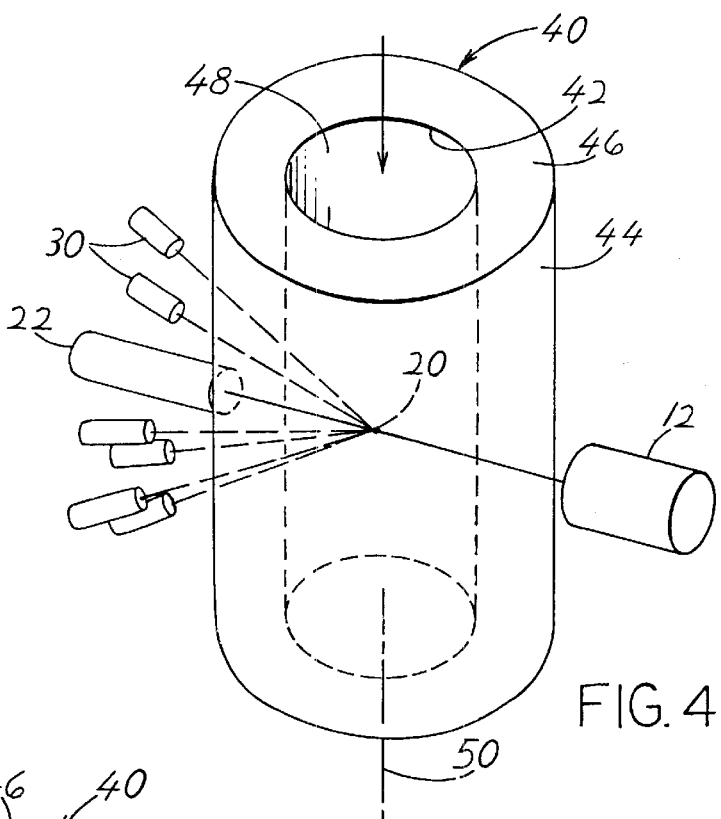
FIG. 4 is an isometric view of a system of one embodiment of the invention.

FIG. 1 shows a scatter detector system 10 which includes a laser 12 that generates a narrow laser beam 14 that passes through fluid 16. One example is a laser beam of red light of a wavelength of 0.6 microns, and a fluid 16 which is water that may contain pathogenic bacteria. Applicant uses the terminal "light" to include wavelengths from infrared to far ultraviolet and even soft x-rays. The laser beam passes through a detect zone 20 to a dump 22 that captures most of the laser beam energy. The fluid moves along the direction of arrow D to carry the particles to be identified, some of which will pass through the detect zone 20 lying along the laser beam. When a particle passes through the detect zone, light of the laser beam is scattered by the particles. The scattered light (including light generated by luminescence) is detected by several detectors such as photodetectors 30. The outputs of the several detectors can be analyzed by a computer program designed to identify the particle. We note that it is useful to merely detect the presence and/or number of particles per unit volume in some applications (e.g. purified water to be used in scientific research).

The detectors 30 can be diodes that change resistance, diodes that generate current, charge coupled diodes, locations on a film, etc. The photodetectors 30 in FIG. 1 lie on two circular rings 32, 34 that lie in perpendicular planes. Each photodetector detects only light received within a narrow angle such 2°, to detect only light originating from the detect zone. Information about the scatter pattern helps to analyze the particles that pass through the detect zone 20.

It is useful to detect the scattering pattern of a variety of particles, including organic and nonorganic materials, bacteria, cells, ice crystals, dust, and minerals. Scattering patterns of particles can be used to classify the particles or to characterize the particles in size, shape, orientation, composition, geometry, and other physical properties. One use for the scatter detector system is to identify species of pathogenic microorganisms found in a water supply.

The system 10 of FIG. 1 can be used to detect particles in water by immersing the system in water. This has many disadvantages, including the fact that the water may corrode parts of the system such as the photodetectors 30 and may coat them with biological films that can form on immersed surfaces. It is often desirable to test a moderately small sample of fluid, so it would be desirable if the fluid passed through a container or carrier of smaller diameter than the entire system 10. Some fluids may contain pathogens, and it is desirable to not contaminate the different components of the system 10 with such pathogens.

FIGS. 2 and 3 illustrate a prior art system G which includes a shell H, a laser 12 and dump 22 aligned with openings in the shell, and a plurality of photodetectors 30 that detect scattering of the laser beam 14 from a detect zone 20 lying along the laser beam. Fluid such as water is passed into the shell through an opening J and exits the shell through another opening K. The fluid paths P bring the fluid to all parts of the shell, including the detect zone 20.

The system G has the advantage that light scattered from the detect zone 20 can reach a photodetector 30 while moving only along a medium of constant index of refraction. The index of refraction for air is 1.0 while the index for water is about 1.33. As a result, each path of scattered light, such as path Q, is a straight line from the detect zone 20 to a photodetector 30. However, the system G has disadvantages, including the fact that the photodetectors 30 are exposed to the fluid in the shell, and may be coated with a biological film, or slime, and may be contaminated with pathogens in the fluid. It can be appreciated that cleaning portions of the photodetectors 30 that project into the shell can be very difficult without removing the photodetectors. Only a very small percent of fluid flowing, through the shell passes through the detect zone 20, since the cross section of the spherical shell in a horizontal plane that includes the laser beam 14, is very large. Accordingly, a large amount of fluid is required to obtain a given number of particle detections. In addition, if a liquid such as water is the fluid that carries the particles, then a rapid flow of water through the shell could result in cavitation where the photodetectors 30 and dump 22 project into the shell, resulting in tiny bubbles that can deflect scattered light.

FIG. 4 illustrates a carrier 40 formed by a glass pipe having cylindrical inside and outside surfaces 42, 44. The laser 12 lies outside the glass pipe and directs a laser beam through one side of the glass wall 46 of the pipe and through the axis 50 of the pipe. The laser passes through fluid such as water lying in the pipe and exits through an opposite side of the wall 46 of the pipe. When a particle passes through the detect zone 20 that lies on the axis of the pipe, light is scattered by the particle and passes through the walls 46 of the pipe and is detected by photodetectors 30 lying outside the pipe. The cylindrical glass carrier 40 provides the advantages that the laser 12, dump 22 and photodetectors 30 are all isolated from fluid in the passage 48 that extends through the glass pipe. Also, the passage 48 can be made to have a moderately small diameter so that a greater proportion of the particles in the fluid will pass through the detect zone, to allow an analysis using a smaller sample of fluid. However, the carrier 40 has certain disadvantages, including the fact that light scattered at a large angle to the horizontal will not pass through the glass wall 46 of the pipe, as explained below.

Figure 5:
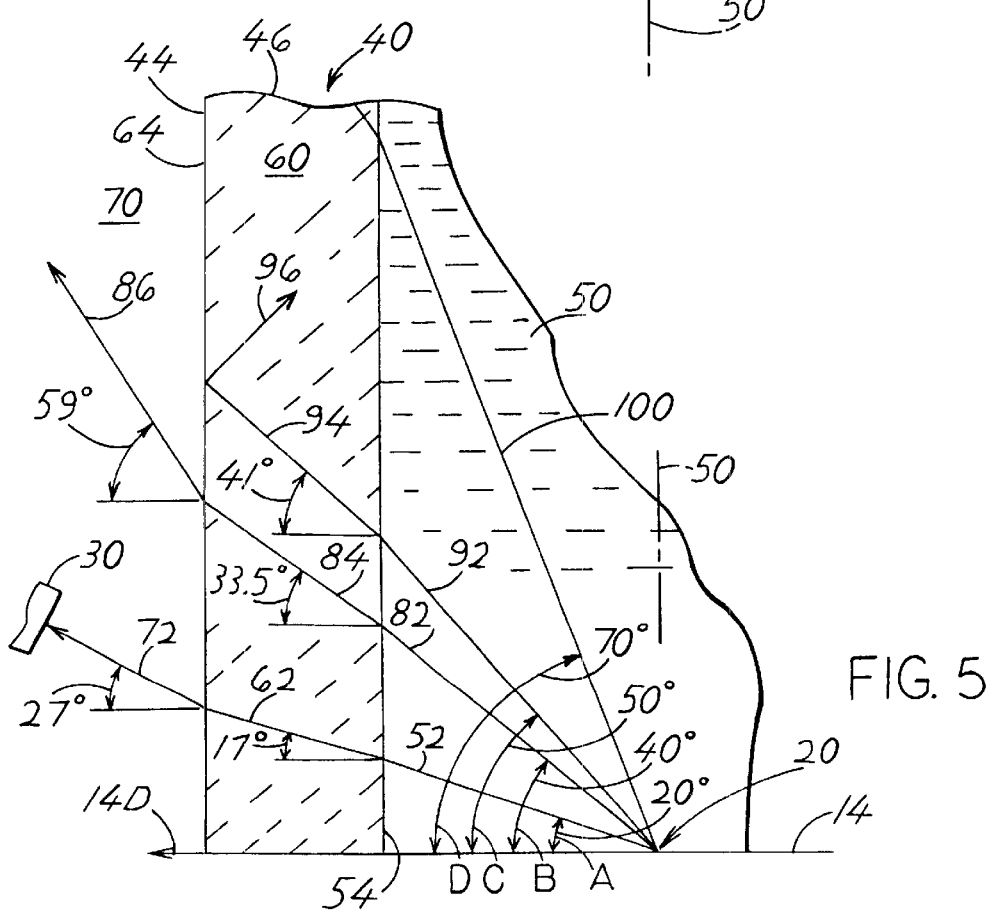
FIG. 5 is a sectional side view of a portion of the system of FIG. 4, showing the paths of scattered light through water, through glass of the carrier, and into air surrounding the carrier.

FIG. 5 shows that paths of light scattered by a particle in the detect zone 20 that lies along the laser beam 14. The laser beam travels along the laser beam direction 14D. The detect zone 20 that particles pass through, lies in water 51 that is contained in the fluid container or carrier 40 whose wall 46 has inside and outside cylindrical surfaces. Light scattered by a particle in the detect zone 20 and that moves along the path portion 52 that is inclined by an angle of 20° from the laser direction, passes through the interface 54 between the water 51 and the glass 60 of the carrier walls. The index of refraction of water is 1.33, while the index of refraction of one common type of glass is 1.55. As a result, the scattered light moves through the glass along a path portion 62 that is angled 17° from the horizontal laser direction. When the scattered light emerges from the interface 64 between the glass and air 70, the light moves along a path portion 72 that is angled by 27° from the laser direction 14D.

Light moving along path portion 72 is detected by one of the detectors 30. Similarly, light scattered from the detect zone 20 and moving at an angle B of 40° from the laser beam direction 14D moves along a path portion 82. The path portion 84 in the glass is angled 33.5° from the laser direction 14D. The light continues in the air along path portion 86 that is angled 59° from the laser direction, to another detector.

Light scattered from a particle at the detect zone 20 at an angle C of 50° from the laser beam direction 14D will move along path portion 92. The light then moves in the glass along path portion 94 which is at an angle of 41° from the laser beam direction 14D. However, when the beam moving along path portion 94 encounters the interface 64 between the glass and air, the beam will be reflected from the container outer surface 44 along path portion 96.

When light passes from a medium of high index of refraction such as glass having an index of 1.55, to a medium of lower index of refraction such as air with an index of 1.0, there is a critical angle beyond which all light is reflected from the interface rather than passing through it. For glass having an index 1.55, the critical angle is 41° at a glass-air interface. For a glass having an index of 1.50, the critical angle is 42°. As a result, in FIG. 5, only light scattered at an C angle less than plus or minus 50° from the horizontal laser beam direction 14D will pass out of the fluid carrier. Important information can be obtained by scattering of light at angles of greater than 50°, and it is desirable that the transparent container allow the detection of light scattered at more than 50° from the beam direction.

FIGS. 6–8 illustrate a container or carrier 110 of the present invention, which enables the laser and photodetectors to lie outside the fluid, while allowing the detection of light scattered at a wide angle from the beam direction. FIG. 6 shows that the carrier has a largely hemispherical convex lens 112. The lens lies in front of walls 114 forming a container or passage 116 in which fluid can be contained or through which fluid can pass, where the fluid contains particles whose scattering patterns are to be detected. FIG. 7 shows that the laser beam 14 generated by the laser 12 passes through a rear wall 120 and through the passage 116, so the laser beam passes through a detect zone 122 lying in the passage. Most of the light passes through the lens 112 to the dump 22. The carrier has a largely parallelopiped shape, with flange portions, which can facilitate mounting it.

FIG. 7 shows the paths of light scattered at different angles from the detect zone 122. Light initially scattered at an angle from the horizontal beam direction 14D is shown which is initially scattered at angles of 20°,40° and 50°, which pass through the glass of the lens at angles of 17°, 33.5°, and 41° (path 104). Light passing along those paths pass through the interface 124 of glass and the surrounding air 70 substantially normal, or perpendicular to the lens outer surface 126.

It is noted that light scattered at an angle approaching 90° to the laser beam direction 14D, such as 80° or more, will be reflected at the interface 130 between the water and glass of the lens, and normally cannot be detected. However, the glass surface of the passage, at the interface 130, can be coated with a nonreflecting coating, to increase the scatter angle that can be detected.

The carrier 110 of FIGS. 6–8 can be constructed, as shown in FIG. 8, of four parts 132, 133, 134, 135 that are joined as by adhesive at 136. It is noted that it is usually desirable to also detect light that is scattered at a downward incline to the horizontal beam direction 14D.

FIGS. 9 and 10 illustrate an apparatus 138 that includes a part spherical lens 140 that has front and rear portions 141, 142. The rear portion lies on a side of the passage 116 opposite the main, largely hemispherical front portion 112 that lies in front of the passage. The rear wall of the passage is also flat. A rear flat spot 144 is provided for the laser beam to enter the lens and a front flat spot is provided where the laser beam exits and reaches the dump 22. The detect zone 122 lies close to the front surface 133 of the passage, so light that scatters at a large angle (e.g. 80°) from the beam direction 14D will reach the interface 130 not far above or below the beam 14. FIG. 10 shows that the center point 150 of the lens front portion 112 lies behind or rearward R of the detect zone. The center point 154 of the spherical lens rear portion 142 lies forward F of the detect zone.

In FIGS. 8 and 10, the laterally-spaced sides 125 of the passages are rounded in half circles that merge tangentially with the flat surfaces, without steps. The purpose is to avoid non-laminar flow which could result in the generation of bubbles that could scatter light and interfere with particle detection. If experiments show that even the rounded edges 125 generate bubbles, then the passage can be widened, as to the shape shown in FIG. 6 at 116A, wherein the edges 127 are widely spaced.

If it is found that even sharp edges do not affect laminar flow, then applicant could use a passage having a cross-section shown in FIG. 11.

FIG. 11 shows a carrier 170 with a passage 172 having flat front and rear walls 174, 176, and also having flat laterally-spaced sides 180, 182. Light scattered within angles A or B that each extend from 0° to about 70° to the laser beam direction 14D pass through the flat front wall 172. Light scattered at angles D, E that are each angled between about 70° and 110° from the laser beam direction 14D pass through the side walls 180, 182. Light that is scattered backward passes through the flat rear wall 176. The passage 172 of FIG. 11 allows the use of a passage of small cross-section, so that a considerable portion (e.g. 5%) of the fluid that flow through the passage actually flows through the detect zone 122. In FIG. 11, the width S, in a lateral L direction, of the front wall is about five times the distance V between the center of the detect zone and the front wall 174. A width S of at least 6 times the distance V allows light at angles A or B of 70° to pass through the front wall. The detect zone can be positioned closer to the front wall 174 than the rear wall.

FIG. 12 shows the shape of the cross section of the laser beam 14, as it passes through the center of the fluid-carrying passage. The laser beam has a moderately small width W such as 1.5 mm and an even smaller average thickness T such as 0.1 mm at the detect zone. FIG. 13 shows a situation where the passage 200 is of cylindrical shape, with a circular cross-section, and where the circular cross-section is only twice as wide as the width W of the laser beam. A cylindrical cross-section allows the passage to be formed in a solid sphere of glass by boring the passage through the solid sphere. However, light from opposite sides of the detect zone 122 diverge considerably due to the small radius of curvature of the passage. FIG. 13 also shows a photodetector 210 lying outside the spherical surface 212 of the glass sphere or hemisphere. It is assumed that the photodetector 210 detects light only within a small angle 216 such as 2° from the detect zone, to detect only light scattered from the small detect zone 122 but not from light scattered from points outside the detect zone. FIG. 13 shows a light ray 220 from the center of the detect zone 122, and shows light rays 222, 224 that originate from laterally opposite sides of the detect zone. The light rays 222, 224 diverge, and along the relatively long path of the glass sphere, the light diverges sufficiently that it is not detected by the photodetector 210. This can be largely avoided by using a cylindrical passage 200 of much larger diameter than the width W of the laser beam, such as at least about 6 times as great. However, this results in a passage of larger cross-sectional area, FIG. 14 shows the path of light originating from the center of the detect zone 122 in passing through the flat front wall 230 of a passage. The light path 240 represents light from the center of the detect zone 122. Light from the laterally opposite sides of the detect zone move along paths 242, 244. Since the passage front surface 230 is flat, the paths 242, 244 are parallel to each other and to the center path 240, so light from opposite sides of the detect zone will be detected by the photodetector 210. The paths of light rays 240–244 are easier to calculate precisely, than the paths of the light rays 220–224 of FIG. 13.

FIG. 15 illustrates another carrier 250 with upper and lower conical surfaces 252, 254 and a cylindrical middle surface 256. The upper surface portion extends at an upward incline and toward the passage axis 260, while the lower surface portion extends at a downward incline and toward the axis, as in the case of a sphere.

FIG. 16 illustrates another carrier 270 which is similar to the carrier of FIG. 6 except that there is no hemispherical convex lens forward of the detect zone 272. Instead, the carrier is formed of two sheets 274, 276 of plate glass separated by spacers 280, 282. For particles having dimensions substantially larger than the laser beam wavelength, it is found that detection within a circle 284 that receives light from the detect zone that is angled up to about 40° from the laser beam direction, is sufficient to accurately identify the particle. However, for smaller particles, a large angle of detection (or smaller wavelength) is required. Thus, the low cost carrier of FIG. 16 is useful in detecting larger particles.

Although applicant shows the fluid moving downwardly, it could be made to flow in any direction, so terms such as "downward", "horizontal", etc. only refer to the apparatus as it is illustrated, but the apparatus can be used in any orientation with respect to the Earth.

Thus, the invention provides a carrier through which fluid containing particles can flow to enable detection and identification of the particles, which separates the laser and photodetectors from the fluid and which confines the fluid to a passage of relatively small cross-section so that a substantial portion of the fluid passes through a detect zone of the laser beam. The apparatus includes a carrier of transparent (to the particular light wavelength used) material such as glass with an outer surface having an upper portion that extends at an upward incline towards that axis of the passage, and a lower portion that extends at a downward incline towards the axis of the passage. The passage can have a front surface that is flat or planar, and the passage can be thin and may even be of small width to minimize its cross-section.

Although particular embodiments of the invention have been described and illustrated herein, it is recognized that modifications and variations may readily occur to those skilled in the art, and consequently, it is intended that the claims be interpreted to cover such modifications and equivalents.

What is claimed is:

1. A system for detecting and identifying microscopic particles, comprising:
   a carrier formed of a solid transparent material, said carrier having a passage through which fluid with particles can pass, said passage having a vertical axis, said carrier defining a horizontal centerplane that is normal to said axis, and said carrier having an outer surface with upper and lower surface portions that are inclined respectively upwardly and toward said axis, and downwardly and toward said axis;
   a light source that generates a beam of light that travels forwardly along said horizontal centerplane and though said axis, and that defines a detect zone where said beam passes through said axis;
   a plurality of photodetectors that lies outside said carrier outer surface and that detect light scattered in different directions from a particle lying in said detect zone;
   said passage having a front wall which is flat.

2. The system described in claim 1 wherein:
   said carrier is formed from a plurality of pieces of glass that are adhesively bonded, including a front piece of glass that has a flat rear surface that forms said passage front wall which is flat.

3. The system described in claim 1 wherein:
   said passage has a rear wall that is flat and parallel to said front wall.

4. The system described in claim 1 wherein:
   said passage has laterally opposite side walls that are each flat and perpendicular to said front wall.

5. A system for detecting and identifying microscopic particles, comprising:
   a carrier formed of a solid transparent material, said carrier having a passage through which fluid with particles can pass, said passage having a vertical axis, said carrier defining a horizontal centerplane that is normal to said axis, and said carrier having an outer surface with upper and lower surface portions that are inclined respectively upwardly and toward said axis, and downwardly and toward said axis;
   a light source that generates a beam of light that travels forwardly along said horizontal centerplane and though said axis, and that defines a detect zone where said beam passes through said axis;
   a plurality of photodetectors that lies outside said carrier outer surface and that detect light scattered in different directions from a particle lying in said detect zone;
   said carrier comprising a plurality of separate pieces of transparent material that is fastened together.

6. The system described in claim 5 wherein:
   at least one of said pieces has a flat rear surface and forms a front wall of said passage.

7. Apparatus for use in a system for detecting and/or identifying microscopic particles in a fluid, which includes a source that generates a light beam that travels along a forward longitudinal direction through a detect zone, and a plurality of photodetectors that detect light scattered in different directions from said detect zone, comprising:
   a carrier constructed of a solid transparent material, said carrier having walls forming a passage extending along a passage axis for carrying the fluid that contains particles, and said carrier walls forming an outside surface, so at least said photodetectors can lie outside said outside surface and detect light from a detect zone that lies along the light beam and in the passage;
   said passage has a front surface which is planar;
   there is a predetermined longitudinal distance between a center of said detect zone and said passage front surface, and said passage has a width in a lateral direction which is at least six times said longitudinal distance, whereby to enable light scattered from said center of said detect zone at an angle of about 70° to said beam path to pass through said planar front surface.

8. Apparatus for use in a system for detecting and/or identifying microscopic particles in a fluid, which includes a source that generates a light beam that travels along a forward longitudinal direction through a detect zone, and a plurality of photodetectors that detect light scattered in different directions from said detect zone, comprising:
   a carrier constructed of a solid transparent material, said carrier having walls forming a passage extending along a passage axis for carrying the fluid that contains particles, and said carrier walls forming an outside surface, so at least said photodetectors can lie outside said outside surface and detect light from a detect zone that lies along the light beam and in the passage;
   said passage has a front surface which is planar;
   said passage has curved laterally spaced side walls that are each concavely curved and that have front ends that are substantially tangential to said front wall.

9. Apparatus for use in a system for detecting and/or identifying microscopic particles in a fluid, which includes a source that generates a light beam that travels along a forward longitudinal direction through a detect zone, and a plurality of photodetectors that detect light scattered in different directions from said detect zone, comprising:
   a carrier constructed of a solid transparent material, said carrier having walls forming a passage extending along a passage axis for carrying the fluid that contains particles, and said carrier walls forming an outside surface, so at least said photodetectors can lie outside said outside surface and detect light from a detect zone that lies along the light beam and in the passage;
   said passage has a front surface which is planar;
   said light beam has a predetermined width in a lateral horizontal direction that is perpendicular to said beam path and to said passage axis, and said passage has a length along said longitudinal direction, which is no more than 4 times said beam width, and said passage has a width in a lateral direction that is perpendicular to said beam path which is no more than four times said width, whereby to enable a considerable portion of the fluid to pass through the detect zone.

* * * * *